(12) United States Patent
Mattson

(10) Patent No.: US 6,455,259 B2
(45) Date of Patent: Sep. 24, 2002

(54) METHODS FOR DETECTING, SELECTING AND CLONING AGENTS THAT DEGRADE OR PROMOTE DEGRADATION OF DNA

(76) Inventor: Thomas L. Mattson, 20220 Tidewinds Way, Germantown, MD (US) 20874

( * ) Notice: Subject to any disclaimer, the term of this patent is extended or adjusted under 35 U.S.C. 154(b) by 0 days.

(21) Appl. No.: 09/903,986

(22) Filed: Jul. 13, 2001

Related U.S. Application Data

(62) Division of application No. 09/261,764, filed on Mar. 3, 1999, now Pat. No. 6,268,139.
(60) Provisional application No. 60/076,657, filed on Mar. 3, 1998.

(51) Int. Cl.[7] .......................... C12Q 1/68; C07H 21/02; C07H 21/04
(52) U.S. Cl. .......................... 435/6; 536/23.1; 536/24.3
(58) Field of Search ....................... 435/4, 6; 536/23.1, 536/24.3

(56) References Cited

U.S. PATENT DOCUMENTS

| | | | |
|---|---|---|---|
| 5,180,673 A | 1/1993 | Wilson et al. | 435/199 |
| 5,200,333 A | 4/1993 | Wilson | 435/172.3 |
| 5,559,018 A | 9/1996 | Mattson et al. | 435/172.3 |
| 6,268,139 B1 | 8/2001 | Mattson | 435/6 |

FOREIGN PATENT DOCUMENTS

| WO | WO 99/45151 | 9/1999 | |
|---|---|---|---|

OTHER PUBLICATIONS

Studzinski et al., Biochem. and Biophys. Research Commun., vol. 25, No. 3, pp. 313–319 (1966) Academic Press.

A. Murata, Nippon Nogei Kagaku Kaishi, vol. 46, No. 3, pp. 147–153 (1972) Abstract Only.

J. Brooks et al., Nucleic Acids Research, "Cloning the BamH1 Restriction Modification System," vol. 17, No. 3, pp. 979–997 (1989) IRL Press.

R. Walder et al., Proc. Natl. Acad. Sci., "Cloning and Expression of the Pst1 Restriction–Modification System in *Escherichia coli*," vol. 78, No. 3, pp. 1503–1507 (1981) National Academy of Sciences.

M. Mann et al., Gene, "Cloning of Restriction and Modification Genes in *E. coli*: The Haball System from *Haemophilus haemolyticus*," vol. 3, No. 2, pp. 97–112 (1978) Elsevier Science BV.

*Primary Examiner*—Ethan C. Whisenant
(74) *Attorney, Agent, or Firm*—Foley & Lardner

(57) ABSTRACT

A method is described for detecting, selecting, and cloning agents that degrade DNA or promote DNA degradation. The method utilizes extra-chromosomal replicons whose replication is dependent on degradation of a host cell's DNA to screen for agents leading to degradation of cellular DNA. An agent which promotes degradation of a host cell's DNA enables the replicons to replicate, which signals the presence of agents that promote the cellular DNA degradation and allows for the isolation and amplification of such agents.

16 Claims, No Drawings

METHODS FOR DETECTING, SELECTING AND CLONING AGENTS THAT DEGRADE OR PROMOTE DEGRADATION OF DNA

This is a Divisional application of U.S. Ser. No. 09/261,764, filed Mar. 3, 1999, now U.S. Pat. No. 6,268,131 and claims the benefit of U.S. Provisional Application No. 60/076,657, filed Mar. 3, 1998.

Some of the research underlying this invention was partially funded by the National Institutes of Health's National Cancer Institute's small business innovative research program grant number 1 R43 CA62681-01.

FIELD

The invention relates to a method for detecting, selecting, and cloning agents that disrupt, degrade or promote degradation of cellular DNA, and novel agents selected by practicing these methods.

BACKGROUND

Agents that disrupt, degrade or promote degradation of DNA are useful in a variety of ways. For example, restriction endonucleases (enzymes which cut DNA at specific sites) are highly useful tools for researchers involved in the manipulation of DNA. Also, DNA-degrading agents are useful to kill cells, for example, cancer cells.

Restriction endonucleases act by recognizing and binding to particular sequences of nucleotides (the "recognition sequence") along the DNA molecule. Once bound, they cleave the molecule within, or to the side of, the sequence. Different restriction endonucleases have affinity for different recognition sequences. More than one hundred different restriction endonucleases have been identified among the many hundreds of bacterial species that have been examined to date.

Bacteria tend to possess at most only a small number of restriction endonucleases per species. The endonucleases typically are named according to the bacteria from which they are derived. Thus, the species *Haemophilus aegyptius*, for example, synthesizes 3 different restriction endonucleases, named Hae I, Hae II and Hae III. Those enzymes recognize and cleave the sequences (AT)GGCC (AT), PuGCGCPy and GGCC respectively. *Escherichia coli* RY13, on the other hand, synthesizes only one enzyme, EcoRI, which recognizes the sequence GAATTC.

In nature, restriction endonucleases play a protective role in the welfare of the bacterial cell. They enable bacteria to resist infection by foreign DNA molecules like viruses and plasmids that would otherwise destroy or parasitize them. They achieve this resistance by scanning the lengths of the infecting DNA molecule and cleaving them each time the recognition sequence occurs. The break-up that takes place disables many of the infecting genes and renders the DNA susceptible to further degradation by non-specific exonucleases.

A second component of bacterial protective systems are the modification genes or methylases. These enzymes are complimentary to restriction endonucleases and they provide the means by which bacteria are able to identify their own DNA and distinguish it from foreign, infecting DNA. Modification methylases recognize and bind to the same nucleotide recognition sequences as the corresponding restricting endonucleases, but instead of breaking the DNA, they chemically modify one or other of the nucleotides within the sequence by the addition of a methyl group. Following this methylation, the recognition sequence is no longer bound or cleaved by the restriction endonuclease. The DNA of a bacterial cell is always fully modified, by virtue of its modification methylases. It is therefore completely insensitive to the presence of the endogenous restriction endonucleases. It is only unmodified, and therefore identifiably foreign DNA that is sensitive to restriction endonuclease recognition and attack.

Cloning DNA that encodes agents disrupting, degrading or promoting degradation of DNA, such as restriction enzymes, has been difficult because such agents can degrade the very DNA in the cells used to isolate them. Indeed, it has been recognized that some failures in restriction endonuclease cloning may be due to this lethality problem (Brooks et al., *Nucleic Acids Research*, 17(1988): 979–997). Some tricks have been developed for isolating this type of DNA, but the strategies developed so far offer only limited success. For example, some investigators have used bacteriophage infection as a means of selectively isolating restriction endonuclease clones (Walder et al., *Proc. Nat. Acad. Sci.*, 74: 1503–1507 (1981); Mann et al., *Gene*, 3: 97–112 (1981)). Since the presence of restriction-modification systems in bacteria enable them to resist infection by bacteriophages, cells that carry cloned restriction-modification genes (R/M) can in principle be selectively isolated as survivors from libraries that have been exposed to phage. This method has been found, however, to have only limited value. Specifically, it has been found that cloned restriction-modification genes do not always manifest sufficient phage resistance to confer selective survival.

U.S. Pat. Nos. 5,180,673 and 5,200,333 to Wilson et al. disclose a method for over-production of restriction enzymes and their corresponding modification enzymes involving the following steps:

1. The DNA of the bacterial species to be cloned is purified.
2. The DNA is digested partially with a convenient restriction endonuclease.
3. The resulting fragments are ligated into a cloning vector, such as pBR322, and the mixture is used to transform an appropriate host cell such as *E. coli* cells.
4. The DNA/cell mixture is plated on antibiotic media selective for transformed cells. After incubation, the transformed cell colonies are scraped together into a single culture, the primary cell library.
5. The recombinant plasmids are purified in toto from the primary cell library to make a primary plasmid library.
6. The plasmid library is then digested to completion in vitro with the restriction enzyme whose corresponding methylase gene is sought. Exonuclease and/or phosphatase may is also be added to the digestion to enhance the destruction of non-methylase clones.
7. The digested pool is transformed into *E. coli* and transformed colonies are again obtained by plating on antibiotic plates. Some of these colonies—secondary cell individuals—may be picked and their DNA analyzed for the presence of the modification and/or restriction genes. The remaining colonies may be scraped together to form a secondary cell library from which a secondary plasmid library may be subsequently prepared.
8. The secondary plasmid library may be redigested with restriction endonuclease (with or without exonuclease or phosphatase) to repeat the selection, leading to the recovery of tertiary cell individuals, tertiary cell libraries and tertiary plasmid libraries.
9. Each round of restriction endonuclease digestion causes selective destruction of non-methylase clones, and results in an increase in the relative frequency of the desired methylase-carrying clones.

10. Surviving colonies among the secondary and tertiary population are picked and analyzed for the presence of the methylase gene. If it is found to be present, they are further analyzed for the simultaneous presence of the restriction gene that is presumed to be linked to the methylase gene.
11. Methylase screening may be performed by four simple tests:
   (a) The recombinant plasmid DNA molecule of the clone may be purified and exposed to the selecting restriction endonuclease to establish that it is resistant to digestion. Provided that the plasmid vector carries several sites for that endonuclease, resistance indicates modification, rather than mutational site loss.
   (b) The recombinant plasmid may be digested with the enzyme initially used to fragment the donor bacterial DNA. The fragments present in the clone should be comprehensible, sufficiently large to encode a methylase gene (i.e., over 1 Kilobase pair) and, most important, common to a variety of independently-formed clones: the same fragment or fragments should be present among all the clones.
   (c) The total chromosomal DNA of the clone may be purified and exposed to the selective restriction endonuclease. If the clone carries the methylase gene, the bacterial chromosome should be fully methylated and, like the plasmid, should be found to be resistant to digestion.
   (d) The cell extract from the clone may be prepared and assayed in vitro for methylase activity. (Methylase protection and radioactive labelling.) Methylase activity should be found.
12. Restriction endonuclease screening may be carried out in two ways:
   (a) The cell extract from the clone may be prepared and assayed in vitro for its ability to digest sensitive DNA. Restriction endonuclease activity should be found.
   (b) The cells themselves may be tested in vitro for their ability to resist phage infection. Resistance to phage infection indicates the presence of a restriction-modification system. However, the above-described method is essentially a method for selecting for methylase activity which is necessary to save the host's DNA from destruction by the endonuclease being cloned. It is only a useful technique when the endonuclease is linked to a methylase or modification gene closely enough to be on the same restriction fragment.

SUMMARY

It is an object of the present invention to detect and selectively clone an agent that damages or kills a cell in a predetermined way (e.g., by DNA degradation). It is also an object of the present invention to identify and selectively clone DNA encoding agents that disrupt, damage, degrade or promote degradation of cellular DNA, including lethal genes and agents that initiate events leading to cellular DNA disruption, damage or degradation. Another object of the present invention is to provide a new method for cloning genes encoding restriction endonucleases and methylases. It is a further object of the present invention to screen and detect DNA disruption, damage or degradation caused by an agent or sample or activity in an agent or sample that leads to DNA disrption, damage or degradation. Yet another object of the present invention is to provide a method of screening for agents essential to a virulent parasite. Another object of the present invention is biological detection and amplification of in vivo DNA damage that can lead to host DNA degradation.

DETAILED DESCRIPTION

Unless specifically indicated otherwise, all references to "a" or "an" are meant to encompass "one or more" throughout the present application.

One embodiment of the present invention relates to a method of detecting or selectively cloning an agent that kills or damges a cell in a predetermined way (e.g., by DNA disruption, damage or degradation) comprising treating a population of cells with an agent to be tested, introducing into the treated population of cells a marker replicon (e.g.,,a parasite such as a bacteriophage) that preferentially reproduces if a cell is damaged or killed in said predetermined way, and detecting whether or not the agent kills or damages any of the cells in said population of cells based on whether or not the marker replicon has reproduced. The agent to be detected may be genetic or non-genetic. If the agent to be detected is genetic (e.g., a library of DNA sequences to be tested cloned into a plasmid), then the marker replicons may recombine with DNA from the agent to be detected in those cells which are killed, allowing selective cloning of a DNA sequence encoding an agent that kills a cell by recovering the replicons that reproduced in the dying cell. The order of treating with the agent to be tested and introducing the marker replicon into the cells is not limited to the order indicated above and may be reversed.

The marker replicon and/or conditions in which the population of cells is grown are chosen so that the predetermined way in which the cell is to be damaged or killed enhances reproduction of the marker replicon. For example, if the predetermined way in which the cell is to be damaged or killed is based on DNA degradation, then it may be desireable to suppress DNA synthesis in the population of cells (e.g., by adding hydroxyurea and not including mononucleotides in the cell culture media) so that reproduction of the marker replicon depends upon degradation of cellular DNA to generate the mononucleotides needed for reproduction.

Alternatively, if reproduction of the marker replicon requires cellular DNA disruption or damage but does not require complete cellular DNA degradation to mononucleotides, it may not be necessary to suppress DNA synthesis in the population of cells in order to promote marker replicon reproduction.

In the most general case, any condition under which the marker replicon will not replicate unless some predetermined kind of event occurs can be used to identify agents that promote the occurence of the predetermined event. In examples provided below the predetermined kind of event involves cell DNA disruption, damage and degradation which produce conditions allowing reproduction of the marker replicon. The predetermined event complements a genetic requirement for marker replicon replication or otherwise provides some function to support reproduction of the marker replicon.

Agents which degrade or promote degradation of cellular DNA, thereby generating mononucleotides, make it possible for a replicon to replicate even though DNA synthesis is suppressed (e.g., by limiting the availability of mononucleotides with hydroxyurea) in a population of cells. The present invention uses replication of an extra-chromosomal replicon as a marker to indicate that an agent is present which disrupts, damages, degrades and/or promotes degradation of cellular DNA under these conditions. The present invention also uses replication of an extra-chromosomal replicon under these conditions to achieve selective cloning of DNA encoding an agent that disrupts, damages, degrades or promotes disruption, damage or degradation of cellular DNA.

In one embodiment, the present invention relates to a method of detecting agents that degrade or promote degradation of cellular DNA sequences comprising treating a population of cells with an agent to be tested, suppressing DNA synthesis in the treated population of cells, introducing into the treated population of cells a marker replicon, and detecting whether or not the agent degrades or promotes degradation of DNA sequences in said population of cells based on whether or not the marker replicon has replicated. The order of treating with the agent to be tested, suppressing DNA synthesis, and introducing the marker replicon into the cells is not limited to the order indicated above and may be changed to any order desired.

The agent to be detected may be genetic or non-genetic.

The marker replicon can be any replicon whose replication can be detected. Preferably, the marker replicon is a bacteriophage that naturally is unable to degrade a host cell's DNA or a bacteriophage that has a mutation rendering it unable to degrade a host cell's DNA because reproduction of a bacteriophage is more convenient to detect than replication of a plasmid when it happens in only a small fraction of cells in the population. More preferably, the bacteriophage that is the marker replicon is a member of the family of related bacteriophage which includes T4. Most preferably, the bacteriophage is T4.

The present invention also relates to a method of selectively cloning a-DNA sequence encoding an agent that disrupts, damages, degrades or promotes disruption, damage or degradation of cellular DNA comprising introducing into a population of cells a library of DNA sequences to be tested that are cloned into a first extra-chromosomal replicon, suppressing DNA synthesis in said population of cells, and selecting extra-chromosomal replicons which have replicated in said cells due to the presence of a DNA sequence encoding an agent that disrupts, damages or degrades or promotes disruption, damage or degradation of cellular DNA. The order of introducing the library of DNA sequences to be tested and suppressing DNA synthesis is not limited to the order indicated above and may be reversed if desired.

The first extra-chromosomal replicon of the above selective cloning method includes any replicon, including plasmids, bacteriophage, and viruses, capable of introducing a desired DNA sequence into a population of cells. Depending upon whether prokaryotic or eukaryotic cells are utilized, the first extra-chromosomal replicon is selected accordingly. For example, certain plasmids and bacteriophage may be used as the first extra-chromosomal replicon when the cells are prokaryotic, but not if the cells are eukaryotic. On the other hand, shuttle vectors may be used which function in both prokaryotic and eukaryotic cell types.

When prokaryotic cells are used, preferably the first extra-chromosomal replicon is a plasmid. Still more preferably, the first extra-chromosomal replicon is a plasmid containing sufficient bacteriophage T4 DNA to permit recombination with the DNA of bacteriophage T4 or containing a T4 replication origin (when the second extra-chromosomal replicon discussed below is a T4 bacteriophage). Most preferably, the plasmid contains both sufficient bacteriophage T4 DNA to permit recombination with the DNA of bacteriophage T4 and a T4 replication origin.

A preferred first extra-chromosomal replicon for eukaryotic cells is a virus or a shuttle vector which can replicate in both prokaryotic and eukaryotic cells. In eukaryotic cells in which both de novo and salvage pathways for DNA synthesis have been suppressed, extra-chromosomal replicons that contained genes able to initiate apoptosis would be preferentially replicated, allowing one to enrich for or select those genes that initiate apoptosis or otherwise degrade or promote degradation of cellular DNA.

In the above selective cloning method, in a preferred embodiment, two extra-chromosomal replicons are employed. The first extra-chromosomal replicon carries the library that includes the DNA sequences to be tested, as discussed above, and is preferably a plasmid. The second extra-chromosomal replicon is preferably introduced into the population of cells in order to rescue the first extra-chromosomal replicons which have replicated due to the presence of a DNA sequence encoding an agent that disrupts, damages or degrades or promotes disruption, damage or degradation of cellular DNA. The second extra-chromosomal replicon may be introduced into the population of cells before or after the first extra-chromosomal replicon. The second extra-chromosomal replicon can be used to rescue plasmids from the dying cells in which DNA replication has been suppressed, for example, by packaging them into transducing phage particles when a bacteriophage is selected as the second extra-chromosomal replicon. Any vector having the ability to rescue the first extra-chromosomal replicons which have replicated (e.g., plasmids) from the dying cells may be used as the second extra-chromosomal replicon.

Preferably, the second extra-chromosomal replicon comprises DNA resistant to the action of the agent that disrupts, damages or degrades or promotes disruption, damage or degradation of cellular DNA, which enhances its ability to rescue the first extra-chromosomal replicons that have replicated. Having resistant DNA prevents the second extra-chromosomal replicon from being disrupted, damaged or degraded by the agent, which means there is more time for it to complete the rescue of the first extra-chromosomal replicons that have replicated.

Still more preferably, the second extra-chromosomal replicon also contains sufficient DNA in common with the first extra-chromosomal replicon to permit recombination between them.

When the cells used in the selective cloning method are prokaryotic, the second extra-chromosomal replicon is preferably a bacteriophage, which naturally is unable to degrade a host cell's DNA or a bacteriophage which has mutation rendering it unable to degrade a host. cell's DNA. Bacteriophage are also preferable because their reproduction is easier to detect than replication of a plasmid when it happens in only a fraction of cells in the population. More preferably, the bacteriophage that is the second extra-chromosomal replicon is a member of the family of related bacteriophage which includes T4. Even more preferably, the bacteriophage is T4. The second extra-chromosomal replicon is most preferably a T4 bacteriophage with inactive denA and denB gene functions. Any mutation, deletion or insertion may be used to render the denA and denB genes inactive. The denA gene encodes the enzyme (endoII) that initiates the degradation/breakdown pathway of DNA which normally results during T4 infection. This enzyme, endoII, makes single strand nicks in the host chromosomal DNA. This normal T4 pathway involves the sequential production of single strand nicks, single strand gaps, double strand breaks and eventually mononucleotides. An even more preferred extra-chromosomal replicon is T4 bacteriophage carrying the afore-mentioned denA mutation along with a dens mutation which enhances recombination between the bacteriophage DNA and DNA sequences present in the cells. A denB mutation also enables the first extra-chromosomal replicon to replicate autonomously after introduction of the second extra-chromosomal replicon provided the first extra-chromosomal replicon contains a T4 replication origin. See U.S. Pat. No. 5,559,018.

The cells utilized in the present invention may be prokaryotic or eukaryotic. A preferred cell type is prokaryotic. A particularly preferred cell type is *Escherichia coli*. A preferred *E. coli* strain is strain MC1061. Other cell strains may be selected according to the goals of the method. In some instances, strains may be desired that degrade particular kinds of methylated DNA, while in others, strains that do not degrade any kind of methylated DNA might be desired. Likewise, in some instances, strains that repair single strand DNA breaks more slowly than the corresponding wild type strain would be preferred, while in others, a strain might be preferred that repairs single strand DNA breaks as fast as or more rapidly than the corresponding wild type strain.

Another preferred *E.coli* strain is EM237 (REF). EM237 is a preferred strain because it contains a mutation, rpoB5081, in the beta subunit of RNA polymerase that reduces growth of T4 denA mutant phage at elevated temperatures. That is, at elevated temperatures in bacteria carrying this mutation, the denA gene becomes a required gene. Thus, employing this mutation or other similiar bacterial mutations accomplishes the same function as employing hydroxyurea in that this makes the T4 denA gene a required gene. Consequently, to carry out the present invention one could equally well employ the combination of T4 denA mutant phage and hydroxyurea or the combination of T4 denA mutant phage and any bacterial strain carrying mutations, like rpoB5081, that reduce reproduction of T4 denA mutants. Both of these combinations create conditions where the T4 denA becomes necessary and thus conditions where the T4 denA gene can be complemented by agents to be tested.

As used herein, the phrase "complements" means to compensate, offset, or correct a genetic or phenotypic defect or trait.

The phrase "in any order" means that the elements of the method may be carried out in any order, including concurrently at the same time.

The phrase "agent that promotes degradation of cellular DNA sequences" encompasses direct and indirect promotion of DNA degradation, including any event that initiates other events which could lead to DNA disruption, damage or degradation. For example, a restriction enzyme is an agent that directly disrupts and damages DNA and thus directly promotes degradation of cellular DNA sequences. On the other hand, a protease that converts an inactive restriction enzyme into an active restriction enzyme is one example of an agent that indirectly promotes degradation of cellular DNA sequences. Both kinds of agents are encompassed by the phrase "agent that promotes degradation of cellular DNA sequences" as used herein. Methylases that normally protect DNA against digestion by the cognate restriction endonucleases are examples of agents that can indirectly promote DNA degradation. For example, when the host cells contain restriction systems that attack methylated DNA, such as the mcr and mrr genes in *E. coli*, methylase action will produce methylated DNA which then becomes a substrate for systems that directly disrupt, damage and degrade methylated DNA. Thus, the mcr and mrr gene products are examples of agents that can promote DNA degradation. Numerous other agents, for example, many mutagens that themselves do not cause DNA breaks but which modify DNA, would indirectly promote DNA degradation in the presence of an enzyme that initiates a repair pathway that includes producing DNA breaks which can promote DNA degradation at least in a T4-infected cell.

Preferred agents that directly promote the degradation of cellular DNA sequences include naturally occurring and mutant restriction endonucleases and any other endonucleases. Also, DNA-degrading antibiotics (such as bleomycin) are preferred agents to be detected or screened according to the present invention.

Other examples of agents that promote the degradation of cellular DNA sequences include enzymes that can methylate DNA in combination with hosts containing Mcr-like or Mrr-like systems for restricting methylated DNA, or mutants of methylases or of the Mcr-like systems having novel properties. The ability to apply the disclosed methods to methyl modified DNA can obviously be extended to other kinds of DNA modifications which can be processed (either by native host genes or by genes deliberately introduced into the host) into cleaved DNA. Thus, with the disclosed principles and methods one could clone genes able to make the DNA cleavages, clone genes that could activate other genes that are the DNA cleavers or identify agents or genes that can produce cleavable DNA substrates.

Alternatively, other kinds of agents can be detected according to the present invention that complement a defect in a replicon. For example, agents, including genetic and non-genetic agents, that allow denA mutant phage T4 to replicate under any of the conditions that make the T4 denA gene necessary can be identified according to the present invention. Thus, agents that overcome the DNA synthesis block imposed by hydroxyurea, such as genes opening up unique biosynthetic pathways for producing deoxymononucleotides could be identified. Likewise, agents that overcome the block to denA mutant phage reproduction that occurs in the absence of inhibitors, such as hydroxyurea, with mutant host strains of bacteria like EM237, can be identified according to the present invention. The present invention extends to the identification of these other kinds of agents, as well as those agents that promote degradation of DNA.

Also, the present invention extends to detecting agents that have the reverse outcome. For example, agents could be detected that function analogous to or mimic hydroxyurea or the rpoB5081 mutation in *E. coli* strain EM237. Instead of screening for the agents that allow the replicon, e.g., T4 denA mutants, to kill or damage a population of host cells, one would instead screen for the agents that allow a population of host cells to survive in the presence of the T4 denA mutants. This alternative application could be used to identify new compounds for drug discovery and to establish additional conditions under which the T4 denA gene becomes essential. These new or additional conditions under which the T4 denA gene becomes an essential gene would in turn allow the search for yet other agents that complemented T4 denA mutants under the newly established condition that made the T4 denA gene essential.

Suppressing DNA synthesis can be accomplished in numerous different ways by blocking any one or combination of the enzymes involved in replication or limiting the availability of necessary reagents. Preferably, DNA synthesis is suppressed by limiting the availability of mononucleotides needed for DNA replication rather than blocking enzymes that assemble nucleotides into a replicated strand of DNA.

Preferably, DNA synthesis in prokaryotic cells is suppressed by applying hydroxyurea to the cells. Suppressing DNA synthesis in eukaryotic cells can be accomplished by suppressing de novo and salvage DNA synthesis pathways. In mammalian systems, a number of de novo DNA synthesis inhibitors, the so-called antimetabolites, are frequently used, blocking different essential enzymes and resulting in cell growth inhibition at various stages in the cell cycle. One of these antimetabolites, hydroxyurea (HU), is the same inhibitor used to preferentially suppress DNA synthesis in prokaryotes, which also blocks the mammalian encoded version of this essential enzyme, ribonucleotide reductase.

Preferably, DNA synthesis in eukaryotic cells is suppressed by applying hydroxyurea and making sure the culture medium contains no source of nucleotides or, if it does contain nucleotides, then it must contain sufficient inhibitors of the transport systems responsible for cellular uptake of such nucleotides from the medium.

Suppressing salvage DNA synthesis in eukaryotic cells is also known per se. Three sources for salvage pathway nucleotides should be suppressed: (i) the media; (ii) host DNA breakdown initiated by the extra-chromosomal replicon's genes or (iii) host DNA breakdown initiated by the host as a response to some experimental condition; generally either the antimetabolite or the extra-chromosomal replicon or an agent harmful to the cell, such as X-rays.

Mammalian cell culture media often contains bovine calf serum, which contains nucleotides that can be transported into cells and support salvage DNA synthesis. This pathway can be suppressed by using dialyzed serum or by using transport inhibitors. If the media contains sufficient nucleotides from the breakdown of DNA in neighboring cultured cells to support DNA synthesis from this exogenous source, transport inhibitors may be required. If host DNA breakdown is initiated by genes encoded by the invading parasite, as is the case for the T4 parasite, it may be necessary to inactivate said gene, especially if, as in the T4 case, said gene encodes a nuclease that directly attacks the host DNA.

If host DNA breakdown is initiated by host encoded genes, this breakdown, which may be host apoptosis, also must be blocked. Several different proteins, such as the Adenovirus E1B 19kD protein or over-production of the host protein Bcl-2, can block apoptosis. Bcl-2 has been used to block apoptosis induced as a host reaction to antimetabolites, such as HU; to viral infection; and other chemotherapeutic agents. This host-induced block, or resistance to apoptosis, is frequently a major problem limiting successful cancer therapies. Resistance to apoptosis, because it blocks degradation of host DNA can be viewed as a block of a potential salvage DNA synthesis pathway, either for a parasite or replicon that could employ the resulting nucleotides for its own replication or even for any host effort at DNA repair, because, by definition, salvage DNA synthesis is the reutilization of nucleotides previously incorporated into some other polynucleotide chain.

This disclosed principle, as applied to apoptosis, is that suppressing both de novo and salvage synthesis pathways can be used as a powerful tool to select for genes that overcome or complement these blocks, thereby providing a powerful tool for understanding and developing various kinds of therapies. In fact, understanding the basis of this resistance to apoptosis and devising approaches to overcoming it are major goals of cancer research, goals that might be advanced by application of the present invention. In particular, identifying genes in the apoptosis signalling pathway that act downstream of the block imposed by Bcl-2-like proteins is an important goal in cancer research. Identification of such genes will aid in mapping the relevant signaling pathways, is likely to provide new cancer therapy strategies and targets, and may even identify potential suicide genes for gene therapy approaches. However, until this invention, there have been no generally applicable genetic selection principles to guide this effort at identifying effector genes, downstream of these various blocks to apoptosis or other genes whose expression or over expression could overcome these blocks to apoptosis. The present invention provides an approach to drug discovery that could identify such therapies.

Still another embodiment of the present invention is a method of selectively cloning a DNA sequence encoding an agent that is essential for reprodction of a virulent parasite comprising, in any order, introducing into a population of cells a DNA sequence or a library of DNA sequences to be tested that are cloned into a first extra-chromosomal replicon, infecting said population of cells with a virulent parasite under a condition for which complementation is sought and which does not permit parasite progeny to be produced, and selecting parasite progeny which contain a DNA sequence that provided the essential function. The condition for which complementation is sought could be a mutation introduced in advance into the virulent parasite which prevents it from producing progeny or the condition for which complementation is sought could be created by selecting a population of cells in which the virulent parasite normally is unable to produce progeny.

The library of DNA sequences to be screened by the present methods can be any library containing virtually any type of DNA desired to be screened. Preferred libraries include DNA sequences from microorganisms known to include or suspected of including restriction endonucleases. Preferred DNA libraries may also be generated by in vitro mutagenesis of a plasmid known to harbor a DNA sequence encoding an agent of interest, such as a restriction endonuclease. Such libraries are useful when the object is to obtain mutant endonucleases having properties different from the naturally occurring endonuclease (e.g., a thermostable mutant which could be selected for by performing the selection process at an elevated temperature). Preferred mutant enzymes to be selected include those having increased activity on their normal DNA substrates and those having altered or completely different DNA substrates, such as restriction endonucleases or their cognate methylases having altered specificities. Other preferred mutants to be selected include agents that do not act on DNA directly, including but not limited to mutant agents that enable synthesis of active nucleases or that activate inactive endogenous restriction endonucleases. Examples of these latter mutants include mutant proteases, mutant chaperones (to stabilize otherwise unstable proteins), mutant elements of the translation system (such as mutant tRNAs or mutant tRNA synthetases) and mutants of the transcription system.

Sometimes it is preferable to perform repeated cycles of selection. That is, the population of extra-chromosomal replicons obtained after one round of selection might be again introduced into an appropriate host cell and the same or a modified process is performed again. This repetition of cycles can be performed until the desired level of enrichment is obtained.

The present invention solves a problem associated with cloning genes encoding DNA degradation-promoting products by providing a method to rescue plasmids only from dying cells in which two main techniques are combined, complementation and transducer phage production. Selective cloning can be accomplished by employing conditions promoting selective parasite reproduction while allowing no reproduction whatsoever of the host organism.

Another way of making this observation is to point out that although several methods currently exist for cloning/ identifying restriction endonuclease genes, none actually takes advantage of this host lethality to positively select for the corresponding potentially lethal genes. In contrast, the present method directly detects DNA disruption, damage and degradation and exploits it to achieve a positive selection.

The selective cloning of a host-lethal gene is accomplished by combining two techniques, complementation and the production of transducing phage. The complementation herein demonstrated is the first time that is has been shown/ documented that the T4 gene in question, the denA gene, can be complemented by non T4 genes (or agents). This is also the first demonstration that complementation of any T4 gene can be combined with transducer production to clone the complementing gene. It should be clear that application of the teachings of this disclosure are not limited to the particulars of the examples.

Transducing particles are a biological way of using phage particles to move plasmids (or bacterial chromosomal DNA) from one bacteria to another. In the context of the present invention, they may be used to move plasmids. A transducing particle is a phage particle into which the plasmid has been packaged and which subsequently can inject the plasmid (and probably other DNA) into a second bacteria where it will function as a normal plasmid. Transducing particle production is an entirely biological technique for the physical separation/purification of plasmid DNA from chromosomal DNA and for introducing specific plasmids into particular host cells. Thus, it is a different technique from the numerous available in vitro methods for purifying plasmid DNA and for introducing plasmids into host cells. The in vitro methods can also be used, but T4 and its transducing particles have several properties that, collectively, make them preferred for the purpose of manipulating genes promoting DNA degradation, such as those encoding restriction endonucleases (see below).

T4 transducing phage, unlike wild type phage, do not kill when they infect. For T4, the most efficient way to produce transducing particles carrying plasmids is to employ phage mutant in the denB gene and plasmids that contain DNA homologous to DNA present in the infecting phage genomes (preferably, but not necessarily, T4 DNA). Under these conditions there are two routes to forming long arrays of tandemly repeated copies of plasmid DNA, the plasmid substrate which can be efficiently packaged into phage particles and become transducing phage.

In one route, homologous DNA and the denB mutation allow plasmid-phage recombination, producing structures in which multiple copies of the plasmid DNA become integrated into phage genomes in linear, tandemly repeated arrays. Alternatively, if the cloned T4 DNA contains a T4 replication origin, and if the infecting phage carry a denB mutation, tandemly repeated plasmid arrays can be synthesized independent of plasmid-phage recombination. In either case, after packaging into phage particles and subsequent injection into another bacteria, circular plasmid molecules can be formed and function normally. Both routes for producing T4 transducing phage are employed here because the plasmids contain a T4 replication origin.

In this kind of host-parasite system, a cloned restriction endonuclease gene, while killing its host, can simultaneously substitute for (complement) the now-essential T4 denA gene. This complementation allows the production of a burst of progeny phage. The transducing phage particles produced in this burst can be used to rescue plasmids from the dying host cells.

By requiring complementation of the essential phage denA mutant, only the rare bacteria carrying the desired cloned lethal gene produce progeny phage. Some fraction of these progeny phage will pick up, and thus essentially rescue, the complementing plasmid-borne genes. The packaged, rescued plasmid can then be transduced (injected) into an appropriate bacteria where it can be identified, maintained, amplified, manipulated or treated as any other cloned gene. Since the transducing phage are produced only in those bacteria containing the complementing, lethal gene, the subsequently recovered plasmids are only those desired. Thus, T4 is preferred because (i) it can be used to rescue plasmids from cells; (ii) its DNA is resistant to the lethal effects of most restriction enzymes; and (iii) the plasmid rescue can be done selectively, that is, only from the dying cells.

Wild type T4 DNA is resistant to most restriction endonucleases. The molecular basis for this resistance is the incorporation of an unusual base, hydroxymethylcytosine (HMC) into T4 DNA, in place of all the cytosines. Normal wild type T4 DNA also has an epigenetic modification, glucose moieties added to the hydroxymethyl group on the HMC bases. However, the major determinant of resistance to restriction endonucleases appears to be the HMC bases, not the added glucose moieties.

The principles of the invention can be illustrated with $E.$ $coli$ as a host cell, the gene encoding EcoRI restriction endonuclease cloned into a plasmid vector as the first extra-chromosomal replicon containing a gene that leads to DNA degradation, and T4 as the second extra-chromosomal replicon. Consider T4 infection of an $E.$ $coli$ culture containing a random plasmid-based library, in which only a fraction of the cells contain the cloned, active and thus lethal EcoRI gene. Further, consider this infection when it is done with phage mutant in both the denA and denB genes and in media containing the inhibitor hydroxyurea (HU). Finally, the first extra-chromosomal replicon, the plasmid cloning vector, also contains a fragment of T4 DNA bearing a T4 replication origin.

In the infected cells that do not contain the cloned restriction endonuclease, the combination of a denA mutation and the drug HU blocks replication of both T4 DNA and plasmid DNA. In contrast, in those infected cells that do contain the cloned, active restriction endonuclease, host DNA is broken down and T4 DNA can replicate (and accumulate, because its DNA is resistant to the restriction enzyme). Under these conditions, plasmid replication, like T4 genomic replication will be initiated by T4-dependent events, either plasmid-phage recombination or plasmid replication initiated at the cloned T4 origin.

That the particular vector containing cloned T4 DNA allows both T4-dependent pathways of plasmid replication to occur in the phage infected cells serves to illustrate the general idea that producing vector DNA resistant to harmful effects of the lethal gene can be accomplished in multiple ways, even in T4 infected cells, including autonomous replication, replication following recombination, and mere physical sequestration in a transducing particle, and that the kinds of DNA so produced and protected is not limited to T4 DNA. This also serves to illustrate the broader principle that during an interval when host reproduction is blocked (here, independently by HU and virulent phage infection) there is more than one way to achieve selective parasite reproduction.

When plasmid DNA, whether replicated or not, becomes packaged into progeny transducing phage particles it becomes sequestered and thus physically separated from lethal endonuclease action. Thus, plasmids containing the cloned lethal gene can become doubly resistant to this lethal activity; biochemically resistant by incorporation of the unusual base (HMC) and physically sequestered by being incorporated into phage particles. Each of these processes is helpful for separating the desired rare clones from the vast majority of unwanted clones. Together they provide a powerful selective tool.

It should be emphasized that it is not necessary to employ transducing phage (or their equivalents) to carry out the teachings of this invention. That is, employing transducing phage are preferable, but are not a necessary component of this invention.

Other methods could also be used to recover the desired cloned fragments; for example, amplification, e.g., by employing PCR (the polymerase chain reaction) of the above-described digest.

The example below with bleomycin demonstrates that this invention can be performed by employing only a single replicon. Host DNA damage may also be biologically recorded by detecting and measuring progeny parasites/replicons that can be distinguished, in some way, from the input phage/parasites. Total viable progeny phage production can be detected and measured. If the yield of viable progeny phage is not sufficient to distinguish then from the input phage, one can employ anti-T4 serum, which can be used to eliminate all input phage not absorbed to bacteria. Viable genetic recombinants, which are virtually non-existent among the input parasites, may be detected by plating the culture lysate on bacteria selective for these recombinants. Transducing phage production is yet another way of distinguishing progeny from input phage.

The reason that the replicon's DNA need not be resistant to the DNA degradation-promoting agent being selected for is that it is possible to remove or effectively suppress the harmful effects of the agent before the replicated replicon is degraded. For example, bleomycin can be identified as a DNA degradation-promoting agent according to the present invention even though it may degrade or promotes degradation of the replicon's DNA as well as the cellular DNA sequences because it can be removed from the culture at the appropriate time by a simple mechanical means, centrifugation, well before phage infection. Thus, for complementing denA mutants, one can use, identify, detect or selectively clone, agents that could promote degradation of both the host chromosomal DNA, and T4 DNA, if it can be removed, diluted or otherwise rendered inactive on-the T4 DNA before it can cause significant damage to the phage infection. In such a case, unlike the situation with a restriction endonuclease, the parasite DNA need not necessarily either be or become "resistant" to the DNA-harmful agent.

Many cancers develop resistance to the apoptotic effects of chemotherapy. Developing methods to overcome this resistance is a major goal in cancer research. In many cases this resistance is known to be caused by the over-production of certain normal cellular proteins. One recent report demonstrates that Bcl-2, Bcl-XL and the Adenovirus E1B19kD protein are equivalent in inhibiting the apoptosis induced by many cytotoxic agents in a number of cell lines. Thus, in mammalian apoptosis as well as in prokaryotes containing restriction endonuclease, nuclease action (activation in mammalian cells or synthesis in prokaryotes) destroys nuclear DNA. It appears as if in some cases the apoptotic nuclease is activated while in other cases it, or an activator, is synthesized, after an apoptotic signal is recognized. In any case, the relevant analogy here is that in both prokaryotes and mammalian cells, chromosome degradation follows activation or synthesis of an endogenous, potentially lethal activity.

The examples below demonstrate that T4 denA mutants can be complemented in two very different ways: by restriction endonucleases R.EcoRI and R.BamHI and by a non-genetic element, bleomycin, an antibiotic known to cause single strand DNA breaks. The normal T4-induced pathway for degradation/breakdown of host chromosomal DNA starts with single strand breaks which are converted into single strand gaps, then into double strand breaks and finally, following exonuclease digestion, deoxymononucleotides are produced. Thus, in molecular terms, when both the de novo and any salvage pathways are blocked, as in denA mutant infection in the presence of HU, there are not enough single stranded nicks, single stranded gaps, double stranded breaks or deoxynucleotides to enable significant progeny DNA synthesis. Consequently, any gene or agent that can increase the number or concentration of any of these pathway components, directly or indirectly, by whatever means, allows complementation of T4 denA mutants. In the case of bleomycin, the issue of whether or not this antibiotic is harmful to T4 DNA (or some other essential feature of T4 growth) may be avoided simply by washing the cells and thus diluting it prior to the phage infection. Thus, to perform this invention it is not necessary that the replicon be or become resistant to the agent or gene of interest.

The present invention is further illustrated by, though in no way limited to, the following examples.

EXAMPLE 1

The experimental design in all the experiments in this example are basically the same. A test plasmid containing a tsR.EcoRI allele (or a control plasmid lacking R.EcoRI) is transformed into *E. coli* , spread on antibiotic-containing plates and incubated overnight at 42∞ C. Cultures, started from drug resistant cells, are grown at 42∞ C. in rich, drug-containing Luria broth media until the cell density is about 108 cells/ml, when the temperature is shifted down to 30–32∞ C. to activate the restriction enzyme. Hydroxyurea is then added to block de novo synthesis of DNA and five minutes later the culture infected with 5–10 phage/cell. Subsequently, at various times the cultures are lysed and progeny phage assayed in appropriate ways. Viable phage are assayed by standard techniques. The assays for transducing phage are quite robust. However, one must infect with a low multiplicity of viable phage to avoid killing any potential transduced cells and the recipient cells must either contain an active methylase gene to protect against active restriction endonuclease or the transduced cells must be grown at elevated temperatures, when employing the temperature-sensitive mutants of R.EcoRI, to inactivate the endonuclease. Generally, a preferred cell type as host/recipient in transducer-assays are cells unable to support growth of viable progeny phage produced during denA complementation. That is, it is preferable to reduce the chance that progeny from viable phage infections will subsequently infect and thereby destroy transduced cells carrying the selected plasmid. Thus, when infecting phage carry nonsense mutants, as in example 1, and a relatively large yield of transducers is produced, a preferred host is one unable to suppress nonsense mutants, as was used to assay the transducers produced in this example. However, this host type is still able to support growth of the viable wild type recombinants produced in this experiment. In contrast, when few transducers are produced, as in example 2, a preferred host cell type for transducer assays is a lambda lysogen, provided that the phage, as employed in this example, carry extended rII deletions that also eliminate the denB gene, such as the deletion employed, NB2226. Lambda lysogens are a preferred host because when infected with rII mutants they do not produce any progeny.

With this experimental design all the cells in a culture contain the potentially lethal activity and this activity is expressed virtually simultaneously in all cells, following temperature shift-down.

The plasmids used in these experiments contain T4 DNA (5.1 kb; 3.6 kb from the EcoRI fragment containing genes 21–23, inserted in the EcoRI site of PBR322, and 1.5 kb from the HindIII fragment containing genes y-25, inserted in the HindIII site of pBR322), two different vector DNAs (4.3 kb of pBR322 and 2.2 kb of pACYC184, joined together at their BamHI sites) and DNA from the EcoRI R/M system (about 2 kb, replacing the ClaI-BamHI region of pACYC184). Each of these plasmids contains three EcoRI sites and thus is susceptible to R.EcoRI attack after temperature shift-down. The test plasmid (the signal) contained an intact R.EcoRI gene while the control plasmid (the noise) contained an interrupted R.EcoRI gene.

Experiment 1: denA Complementation

In this experiment the bacterial host cannot suppress nonsense mutations, the concentration of HU was 50 mM, the permissive temperature was 30∞ C, and the time of cell lysis 62 minutes (tsEcoRI) or 87 minutes (no EcoRI). All the infecting phage contained a denB deletion (deletion Sa9; to allow transducer production) and an amber mutation in an essential phage gene (g23amA489), a wild type copy of which is on the plasmid. The denA mutation, S112 was employed. In the bacteria used, expression of the cloned product (gp23) is essential for progeny phage production and the wild type allele can recombine into viable progeny phage genomes, giving viable T4 recombinants which can be detected. Thus, in this kind of experiment three different kinds of progeny phage particles can be biologically detected: transducing phage, viable wild type recombinants and total viable progeny.

In this experiment the titer of transducing particles was assayed in cells lacking M.EcoRI (the corresponding methylase for R.EcoRI) and the transduced cells were incubated at 42∞ C. to inactivate the R.EcoRI (restriction endonuclease EcoRI). The test plasmid (the signal) contained an intact R.EcoRI gene while the control plasmid (the noise) contained an interrupted R.EcoRI gene.

As can be seen in experiment no. 1, complementation can be detected as an effect on total viable progeny, viable am+recombinants or as transducers. The magnitude of the effects seen in this experiment, especially on transducing phage, have several independent causes. For total viable progeny, unabsorbed input phage substantially contribute. However, for the recombinants and transducers, types not present in the input phage, other factors are important. The signal/noise ratios observed in this experiment could be improved either by decreasing the noise or increasing the signal. Experiments no. 2 and 3 are concerned primarily with decreasing the noise.

Experiment 2: Time Course of Transducer Production

This experiment differs from the previous experiment only in that aliquots of the culture were lysed at different times after infection. The latest time points give a signal/noise ratio of about 7 but at the earliest time points the signal/noise ratio may be at least 10,000.

Experiment 3: Effect of Hydroxyurea Concentration of Transducer Production

In this experiment, different concentrations of hydroxyurea were tested and the cells lysed after either 50 or 60 minutes. Only transducer yield data is presented. Here it can be seem that the background, but not the signal level of transducers are reduced about 10-fold by increasing the concentration of HU to 200 mM. Higher levels of HU have not yet been tested but likely would further reduce the background, presumably by further reducing the amount of salvage pathway DNA synthesis in the control cells. By combining the results of experiments two and three, it seems that the selective power of this T4-based method, as presently employed, is likely to be at least 100,000-fold. It is clear that this system already has considerable selective power. Although additional improvements in selective power can be achieved by further lowering the background, the largest improvements may be obtained with increases in the absolute numbers of transducers. Using a lysate from an experiment similar to that described in experiment no. 1, a number of additional controls firmly established that the drug resistant colonies obtained after transduction were indeed produced in the expected manner and had the expected properties.

- No colonies were produced if the phage lysate was treated with T4 anti-sera, indicating their T4 phage particle-dependence.
- No colonies were obtained if the infected cell lysate was spread directly on the drug containing plates, demonstrating that no drug resistant colonies survived phage infection and lysis.
- Treatment of the lysate with DNAse did not destroy the transducing ability of the lysate, indicating that the drug-resistant colonies were not the result of transformation of the target cells by free plasmid DNA present in the lysates.
- The transduced colonies were temperature-sensitive for growth, indicating that they contained a temperature-sensitive lethal gene.
- Plasmid DNA isolated from the transduced cells was identical to the starting DNA as judged by restriction enzyme digest patterns.

| SIGNAL | PROGENY YIELD | RATIO SIGNAL/NOISE |
| --- | --- | --- |
| Data for experiment number 1: | | |
| tsEcoRI/30o/denA – | | |
| total viable | 1.9.108 | |
| am+ MR recombinants | 1.2.107 (6.3%) | |
| transducers | 2.7.105 | |
| NOISE/NEGATIVE CONTROL (at 30o: no ecoRI) | | |
| no EcoRI/30o/denA – | | |
| total viable | 1.3.106 | 146 |
| am+ MR recombinants | 3.3.104 (2.5%) | 363 |
| transducers | 3.5.104 | 7.6 |

-continued

| SIGNAL | PROGENY YIELD | RATIO SIGNAL/NOISE |
|---|---|---|
| NEGATIVE CONTROL (at 42o: inactive EcoRI) | | |
| tsEcoRI/42o/denA − | | |
| total viable | 7.4.106 | |
| am+ MR | | |
| recombinants | 4.4.105 (5.9%) | |
| transducers | 8.0.104 | |
| POSITIVE CONTROL (a) (at 30o: active EcoRI/active denA gene) | | |
| tsEcoRI/3Oo/denA + | | |
| total viable | 9.2 × 108 | |
| am+ MR | | |
| recombinants | 4.6 × 107 (5.0%) | |
| transducers | 6.O × 105 | |
| POSITIVE CONTROL (b) (at 30O: no EcoRI/active denA gene) | | |
| no EcoRI/30o/denA + | | |
| total viable | 1.2 × 109 | |
| am+ MR | | |
| recombinants | 1.0 × 108 (8.3%) | |
| transducers | 5.5 × 106 | |

Data for experiment number 2.

_1

Data for experiment number 3:

relative transducer Signal/Noise ratios

| HU conc. | yields at 50 min | 50 min | 60 min |
|---|---|---|---|
| 50 mM | 1.0 | 148 | 34 |
| 100 mM | 1.0 | 760 | 29 |
| 150 mM | 1.0 | >1400 | 250 |
| 200 mM | 0.5 | >1400 | 613 |

EXAMPLE 2

The principles demonstrated in example one, using R.EcoRI as the model system, are here applied and validated by cloning the BamHI R/M system. This R/M system has previously been cloned. This system was chosen as an example of how to apply the disclosed principles because this R/M system meets one of the stated criteria for applying these principles. That is, when both the restriction endonuclease and methylase genes are simultaneously introduced into an non-methylating host, the methylase never wins the kinetic race, killing the host cells. This kinetic race occurs whenever both the endonuclease and cognate methylase are introduced simultaneously into a host cell lacking methylated DNA. Unless the methylase protects the host DNA against endonuclease digestion, that is "wins the kinetic race", the host cell will die and the endonuclease-encoding DNA will be lost. Thus, existing methods for cloning restriction endonuclease-encoding genes require host cell survival and consequently only minimal, if any, host DNA digestion. In contrast, the disclosed method enables selective cloning even when the methylase loses the kinetic race. In fact, the disclosed method takes advantage of the ability of restriction endonucleases to promote DNA degradation to achieve a positive selection for these host-lethal genes.

The BamHI R/M system was originally cloned in a two-step procedure, using two compatible plasmids. First the methylase gene was cloned. The second step was to make a plasmid library in a compatible plasmid in cells already carrying the active methylase, to insure that the host cells were pre-protected, to block killing by the endonuclease activity. Several pools of cells from this library were assayed for endonuclease activity. One endonuclease producing colony out of the original 350 examined contained the BamHI endonuclease.

The 350 colonies that were divided into seven pools, of 50 colonies each, were not from a completely random library. From other studies, hybridizations of radiolabelled probes to Southern Transfers of HindIII digested genomic DNA, it was known that the R.BamHI gene would likely be on a HindIII fragment of about 5 kilobases. Thus, a "limited" library was made from agarose gel purified HindIII restriction fragments of approximately 5 kb, using pACYC184 as the vector. This strategy was copied here to produce a "limited" library of 5 kb HindIII fragments in a vector, pTM83, also derived from pACYC184. In pTM83 the HindIII-BamHI fragment of pACYC184 has been replaced by the slightly larger, approximately 500 bp HindIII-BglII fragment of T4 DNA containing gene 25 and a T4 replication origin. The "limited" library made here, employing standard techniques, like the one originally made to clone R.BamHI, was transformed and amplified in an E. coli strain (RRI) already containing M.BamHI. The M.BamHI bearing plasmid used here to pre-protect the host DNA is a derivative of pSP64 (Promega) having M.BamHI inserted between the HindIII and SmaI sites and an additional oligonucleotide, containing NotI and SfiI sites, inserted at the NheI.

However, after making this "limited" library, the present approach differs significantly from the original approach, which was to directly assay pooled cell extracts for endonuclease activity. Here, total plasmid DNA is purified and separate aliquots treated with either NotI or SfiI restriction endonucleases prior to re-transformation into fresh bacterial cells. These digestions, followed by treatment with PLASMID-SAFETM nuclease (Epicenter) is done to ensure that cells transformed with those rare plasmids containing the complete BamHI R/M system will be host-lethal. That is, following this enzyme treatment these rare cells will not also receive a second viable plasmid bearing only the methylase gene, which could reduce the killing potential of the complete R/M system. More specifically, NotI and SfiI will linearize the pSP64 derivative containing M.BamHI, but allow plasmids from the "limited" library to remain circular. NotI and SfiI were chosen for the task of linearizing the pSP64 protecting plasmid because their recognition sites consist of eight base pairs. That is, by cutting separate aliquots with one or the other of these enzymes it is unlikely that any restriction fragment containing the BamHI or an unknown R/M system would be completely eliminated from the "limited" library.

To be eliminated it would have to be cut in both aliquots; that is, by both of these eight base cutters. (The vector for constructing the "limited" libraries, pTM83 does not, of course, contain either of these sites and thus is resistant.) Thus, when this processed digest is re-transformed into bacteria lacking protective methylation, those rare cells receiving the complete BamHI R/M system will be killed and the host-lethal plasmids can be recovered just as described above in example number one.

When 1 microliter of DNA from such a processed digest was electroporated into electrocompetent E. coli MC1061 cells, about 10% of the viable cells were transformed with the pACYC184 related vector containing the "limited" library, about 100-fold greater than the number of cells receiving the pSP64 related vector containing only M.BamHI. Thus, the NotI and SfiI digestions effectively assured that any cells containing the complete BamHI R/M system would be able to kill their host cells and provide the conditions allowing selection for the cell death genes.

To demonstrate selective cloning of the BamHI R/M system a culture thus transformed was grown at 30∞ C. for 120 minutes, when HU was added to 200 mM and infected five minutes later with phage as described in example one, except that the phage were not mutant in gene 23 and the denB mutation was the extended rII deletion NB2226. The infected cells were lysed after an hour. 0.1 ml of the lysate was assayed for transducing phage on two different hosts, MC1061 lambda lysogen containing or lacking a pBR322 derivative plasmid containing M.BamHI. Ten colonies were recovered with the host containing the protective plasmid while no colonies were recovered with the host unable to protect against killing by the complete BamHI R/M system. The host cells unable to protect against BamHI R/M killing serves as a control for any nonspecific host DNA breakdown that can lead to transducer production. No non-specific background of transducer production was detect when assaying this amount of lysate. Plasmid mini preps were made from the 10 colonies containing the pre-protected host cells. Of the seven cultures that yielded sufficient DNA for restriction digestion analysis, six gave identical digest patterns. (The other miniprep did not appear to digest at all and thus may be completely uninformative.) The digest pattern obtained was that expected if the complete BamHI R/M system had been cloned. One of these six was randomly chosen and a larger culture grown, harvested, lysed with a French Press and examined for BamHI endonuclease activity in fractions eluting from an activated phosphocellulose column. R.BamHI activity was found, in roughly the same amount as reported in the original cloning.

In the prior art's isolation of the BamHI R/M system, one colony out of the 350 examined in the "limited" library was positive. In the present example, the only colony examined for R.BamHI activity, which appeared identical to six out of seven analyzed at the DNA level, was positive for R.BamHI activity. If one assumes that the complexity of the "limited" libraries made in the prior art isolation and in this example were roughly the same, say about one in 350, then it is clear that the disclosed method works very well indeed: it can select one out of 350 with 100% success. At the level analyzed, there is no background of non-specific transducers.

EXAMPLE 3

In this example, a T4 denA mutant phage is complemented with an antibiotic known to cause single strand breaks in DNA, bleomycin. In this example, the production of any viable progeny phage above the background will be evidence of complementation. E. coli strain MC1061, growing at 32∞ C in Luria Broth plus 0.2% glucose was treated for 60 minutes with 10 µg/ml of bleomycin, which was then removed by centrifuging the cells and re-suspending them in an equal volume of the same media. Under these treatment conditions, cell viability is reduced to about 40–50% of that at the beginning of the treatment. The cells are then allowed to grow for various amounts of time at 32∞ C. in the absence of bleomycin, at which times HU is added to 200 mM.

Phage mutant in both the denA and denB genes is added five minutes later. Unadsorbed input phage are eliminated by treating the infected cultures with anti-T4 sera added 15-20 minutes after infection. This anti-T4 sera treatment to eliminate unadsorbed input phage allows detection of a lower level of progeny phage production. However, the anti-T4 sera must be removed or it will also inactivate progeny phage. This was done by centrifuging the infected cultures 50 minutes after infection, washing the pellets with one-tenth volume of media, centrifuging again, re-suspending the culture in one volume of media and immediately causing lysis of the productive cells by the addition of chloroform.

Progeny phage production was assayed by standard methods. A control infection was also done on cells given no bleomycin treatment.

| length of outgrowth | progeny titre/ml | factor increase |
| --- | --- | --- |
| Control (no Bleomycin) | 2.102 | — |
| 0 minutes | 2.6.105 | 1300 |
| 20 minutes | 2.6.106 | 13000 |
| 40 minutes | 4.8.106 | 24000 |
| 60 minutes | 9.0.106 | 45000 |

Thus, with an agent that produces a modest two-fold effect on total cell viability, one can observe more than a 10,000-fold increased titre of an organism whose reproduction can be made dependent on the cellular damage caused by the agent. That is, measuring the effect on the production of progeny phage can be several orders of magnitude more sensitive than measuring the killing effect on the host. This method also appears to detect some kind of a time-dependent conversion of, possibly some kind of DNA lesion to a different form that can be more easily exploited by the phage.

It will be apparent to those skilled in the art that various modifications and variations can be made to the method of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A method of selectively cloning a DNA sequence encoding an agent that degrades or promotes degradation of cellular DNA comprising, in any order, introducing into a population of cells a library of DNA sequences to be tested that are cloned into a first extra-chromosomal replicon, suppressing DNA synthesis in said population of cells, and selecting extra-chromosomal replicons which have replicated in said cells due to the presence of a DNA sequence encoding an agent that degrades or promotes degradation of cellular DNA.

2. The method of claim 1 wherein a second extra-chromosomal replicon is introduced, before or after the first extra-chromosomal replicon, into the population of cells to rescue the first extra-chromosomal replicons which have replicated.

3. The method of claim 2 wherein the second extra-chromosomal replicon comprises DNA resistant to degradation by the selected agent.

4. The method of claim 3 wherein the second extra-chromosomal replicon is selected from the group consisting of plasmids, bacteriophage, and viruses.

5. The method of claim 4 wherein the second extra-chromosomal replicon is a bacteriophage incapable of degrading DNA in said population of cells.

6. The method of claim 5, wherein the bacteriophage is a T4 bacteriophage with impaired denA gene function.

7. The method of claim 6, wherein the T4 bacteriophage further has impaired denB gene function which enhances recombination between bacteriophage DNA and DNA sequences present in the cells.

8. The method of claim 7, wherein the cells are *E. coli* cells.

9. The method of claim 1, wherein the cells are eukaryotic and the first extra-chromosomal replicon is an adenovirus vector that also carries a selectable drug marker.

10. The method of claim 1, wherein the agents that degrade or promote degradation of cellular DNA sequences directly degrade said DNA sequences.

11. The method of claim 10, wherein the library of DNA sequences contains one or more DNA sequences encoding an endonuclease.

12. The method of claim 11, wherein the library of DNA sequences is obtained by mutagenizing a plasmid bearing a DNA sequence encoding an endonuclease prior to introduction of the library into said population of cells.

13. The method of claim 1, wherein the library of DNA sequences is suspected of containing one or more DNA sequences encoding an agent that indirectly leads to cellular DNA degradation.

14. The method of claim 13, wherein the agent converts an inactive restriction enzyme into an active restriction enzyme.

15. The method of claim 1, wherein the library of DNA sequences is suspected of containing one or more DNA sequences encoding a DNA-degrading antibiotic.

16. The method of claim 1, wherein DNA synthesis in said cells is suppressed by contacting them with hydroxyurea.

* * * * *